(12) United States Patent
Schröer et al.

(10) Patent No.: US 11,589,741 B2
(45) Date of Patent: Feb. 28, 2023

(54) ENDOSCOPE AND ENDOSCOPE ASSEMBLY

(71) Applicant: SCHÖLLY FIBEROPTIC GMBH, Denzlingen (DE)

(72) Inventors: Stefan Schröer, Freiburg (DE); Matthias Kühn, Freiburg (DE); Johannes Bourbon, Freiburg (DE); Lutz Labusch, Emmendingen (DE); Michael Schwärzle, Denzlingen (DE)

(73) Assignee: SCHÖLLY FIBEROPTIC GMBH, Denzlingen (DE)

( * ) Notice: Subject to any disclaimer, the term of this patent is extended or adjusted under 35 U.S.C. 154(b) by 0 days.

(21) Appl. No.: 17/094,999

(22) Filed: Nov. 11, 2020

(65) Prior Publication Data
US 2021/0152786 A1 May 20, 2021

(30) Foreign Application Priority Data

Nov. 18, 2019 (DE) .......................... 102019131076.8

(51) Int. Cl.
| | |
|---|---|
| *A61B 1/012* | (2006.01) |
| *A61B 1/07* | (2006.01) |
| *H04N 7/18* | (2006.01) |
| *H04N 5/225* | (2006.01) |
| *H04N 5/235* | (2006.01) |
| *A61B 1/00* | (2006.01) |
| *A61B 1/06* | (2006.01) |

(52) U.S. Cl.
CPC ............ *A61B 1/07* (2013.01); *A61B 1/00126* (2013.01); *A61B 1/00128* (2013.01); *A61B 1/00165* (2013.01); *A61B 1/06* (2013.01); *H04N 5/2253* (2013.01); *H04N 5/2254* (2013.01); *H04N 5/2256* (2013.01); *H04N 5/2354* (2013.01); *H04N 7/183* (2013.01); *H04N 2005/2255* (2013.01)

(58) Field of Classification Search
CPC .... H04N 7/183; H04N 5/2253; H04N 5/2256; H04N 5/2354; H04N 5/2254; H04N 2005/2255; A61B 1/00165; A61B 1/06; A61B 1/00126; A61B 1/00128
See application file for complete search history.

(56) References Cited

U.S. PATENT DOCUMENTS

| 5,589,874 | A | * | 12/1996 | Buchin | ................... A61B 1/042 348/588 |
|---|---|---|---|---|---|
| 5,733,246 | A | * | 3/1998 | Forkey | ................. H04N 5/2256 348/E5.029 |
| 5,913,817 | A | * | 6/1999 | Lee | ......................... H04N 5/378 348/E5.079 |
| 10,986,321 | B1 | * | 4/2021 | Hedges | .................... H04N 9/73 |

(Continued)

*Primary Examiner* — Howard D Brown, Jr.
(74) *Attorney, Agent, or Firm* — Grogan, Tuccillo & Vanderleeden, LLP

(57) ABSTRACT

An endoscope assembly has an endoscope, having an optical waveguide and having an image guide, wherein the image guide is configured to be uninterrupted up to its proximal end and has an image guide interface at its proximal end for optical connection to an image capturing unit, an illumination unit having a light source and having an optical waveguide interface for optical connection of the light source to an optical waveguide, and an image capturing unit having an image sensor and having an image guide interface for optical connection of the image sensor to an image guide.

16 Claims, 3 Drawing Sheets

(56) References Cited

U.S. PATENT DOCUMENTS

| | | | |
|---|---|---|---|
| 2001/0056282 A1* | 12/2001 | Sonnenschein | A61B 17/0686 606/139 |
| 2003/0163029 A1* | 8/2003 | Sonnenschein | A61B 17/0686 600/160 |
| 2004/0133073 A1* | 7/2004 | Berci | A61B 1/07 600/112 |
| 2008/0021273 A1* | 1/2008 | MacKin | A61M 16/0488 600/109 |
| 2009/0043167 A1* | 2/2009 | Leiner | A61M 13/003 600/156 |
| 2011/0187455 A1* | 8/2011 | Sun | H04L 27/368 330/149 |
| 2014/0012081 A1* | 1/2014 | Juergens | A61B 1/04 600/109 |
| 2014/0357951 A1* | 12/2014 | Muller | A61B 1/00045 600/111 |
| 2016/0095507 A1* | 4/2016 | Uram | A61B 1/07 600/108 |
| 2016/0235278 A1* | 8/2016 | Goebel | G02B 23/2469 |
| 2019/0246027 A1* | 8/2019 | Kuhn | A61B 1/051 |
| 2021/0022588 A1* | 1/2021 | Schultheis | G02B 6/3624 |

* cited by examiner

ENDOSCOPE AND ENDOSCOPE ASSEMBLY

CROSS REFERENCE TO RELATED APPLICATION

This application claims priority to German Patent Application No. 10 2019 131 076.8 filed Nov. 18, 2019, which is hereby incorporated by reference in its entirety.

FIELD OF THE INVENTION

The invention relates to an endoscope having an optical waveguide and having an image guide, and an endoscope assembly with such an endoscope.

BACKGROUND OF THE INVENTION

Endoscopes with image guides are well-known in the art. The image guide can be used to transmit an image to an image sensor arranged outside of the endoscope. Compared to an arrangement of the image sensor within the endoscope, this has the advantage that the endoscope can be manufactured at lower costs.

However, after use, endoscopes require considerable treatment and sterilization. Therefore, an object of the invention is to provide an endoscope of the aforementioned type which is altogether easier to handle.

SUMMARY OF THE INVENTION

This object is achieved according to embodiments of the invention by an endoscope having the features of claim 1.

Accordingly, in the endoscope according to the invention, the image guide is configured to be uninterrupted up to its proximal end and has an image guide interface at its proximal end for optical connection to an image capturing unit. In this way, the endoscope can be separated from an image capturing unit in which an image sensor may be arranged, for example. Thus, an image capturing unit may be used with multiple, also different, endoscopes. In particular, it may thus be possible to even switch endoscopes during use without having to change the remaining imaging and image rendering.

In addition, cleaning and disinfecting the endoscope becomes easier. As there is no image sensor arranged within the endoscope, it may also be designed to be so cost-effective that it is suitable for single use and thus does not require any treatment.

In addition, the image guide may be uninterrupted and thus not influence image quality up to a non-sterile area. Thus, the image interface can be configured for maximum image quality as it does not have to be configured to be sterile or sterilizable.

Finally, approval of the endoscope may also be simplified, in particular with combinations of different endoscopes and image capturing units.

The image guide is preferably configured to be flexible, facilitating its introduction into different body orifices and/or body cavities. To this end, the image guide has at least one image guide fiber or at least one image guide fiber bundle.

In one advantageous embodiment, the image guide has two image channels formed by two image guide fibers or two image guide fiber bundles. For example, these two image channels can be used to transmit a stereoscopic image or two images in different spectra.

In one embodiment, the endoscope has a handle, and the image guide extends outward from the handle, in particular at the proximal end of the handle. What is important in the invention is that the image guide runs uninterrupted and without couplings up to the endoscope tip. Accordingly, there is also no interruption of the image guide arranged within the handle. Of particular advantage is here that the image guide interface is arranged within a non-sterile area of the endoscope in any case.

Conveniently, the image guide interface has a coupling for optical and/or mechanical connection to an image capturing unit. The mechanical connection may have, for example, a bayonet coupling, a latching mechanism, a screw connection or another known mechanical connection. In particular, the optical connection may be configured such that the image guide is directly coupled to an image sensor. However, the optical connection may also have an additional image guide within the image capturing unit which is coupled planar and normal to the image guide of the endoscope.

In one embodiment, the endoscope has a light source coupled to the optical waveguide. Preferably, this light source may be arranged in the or a handle of the endoscope.

In an alternative embodiment, the image guide is configured to be uninterrupted up to its proximal end and has an optical waveguide interface at its proximal end for optical connection to an illumination unit.

It is particularly advantageous if the optical waveguide has a coupling for optical and/or mechanical connection to the illumination unit.

In particular, the optical waveguide may substantially have the same length as the image guide.

The invention further comprises an illumination unit for an endoscope assembly, having a light source and having an optical waveguide interface for optical connection of the light source to an optical waveguide.

The illumination unit may be configured to be separate or together with an image capturing unit.

For example, the illumination unit can be arranged within a handle of an endoscope. As such, the illumination unit may have a battery or rechargeable battery for power supply, for example.

The illumination unit may preferably have an electrical interface for controlling the light source. For example, the electrical interface may be configured for connection to a control unit and/or comprise a media interface, in particular USB and/or HDMI interface, for connection to an image display unit, in particular a smart TV.

The invention further comprises an image capturing unit for an endoscope assembly, having an image sensor and having an image guide interface for optical connection of the image sensor to an image guide.

Preferably, the image guide interface has a coupling for optical and/or mechanical connection to an image guide. As such, in particular, the image sensor may be arranged within the coupling area such that it can capture an image of the image guide directly.

In one embodiment, the image capturing unit has an electrical interface for controlling the image sensor and/or for output of the image data of the image sensor. For example, the electrical interface may be configured for connection to a control unit and/or comprise a media interface, in particular USB and/or HDMI interface, for connection to an image display unit, in particular a smart TV.

The invention further comprises an endoscope assembly with an image capturing unit according to the invention, with an illumination unit according to the invention and with an endoscope according to the invention.

The advantage of the endoscope assembly is the modular exchangeability and combinability of the individual components, also during use. Thus, an illumination unit can be readily replaced, for example if illumination in another spectrum is necessary or desired.

The endoscope may also be exchanged, for example if other optics are required.

Hence, the endoscope assembly according to the invention is substantially safer and more flexible to use.

In one embodiment of the invention, the image guide of the endoscope is configured to be uninterrupted up to its proximal end and has an optical waveguide interface at its proximal end for optical connection to an illumination unit.

In one alternative embodiment, the endoscope has a handle and the illumination unit is arranged within the handle.

In one embodiment, the illumination unit and/or the image capturing unit has an interface for connection to a camera control unit.

In one alternative embodiment, the illumination unit and/or the image capturing unit has an electrical interface, in particular USB and/or HDMI interface, for connection to an image display unit.

The image capturing unit and the illumination unit may each be configured as stand-alone devices or arranged in a device.

BRIEF DESCRIPTION OF THE DRAWINGS

The invention will now be explained in greater detail by way of exemplary embodiments with reference to the accompanying drawings.

DETAILED DESCRIPTION

Figure 1:
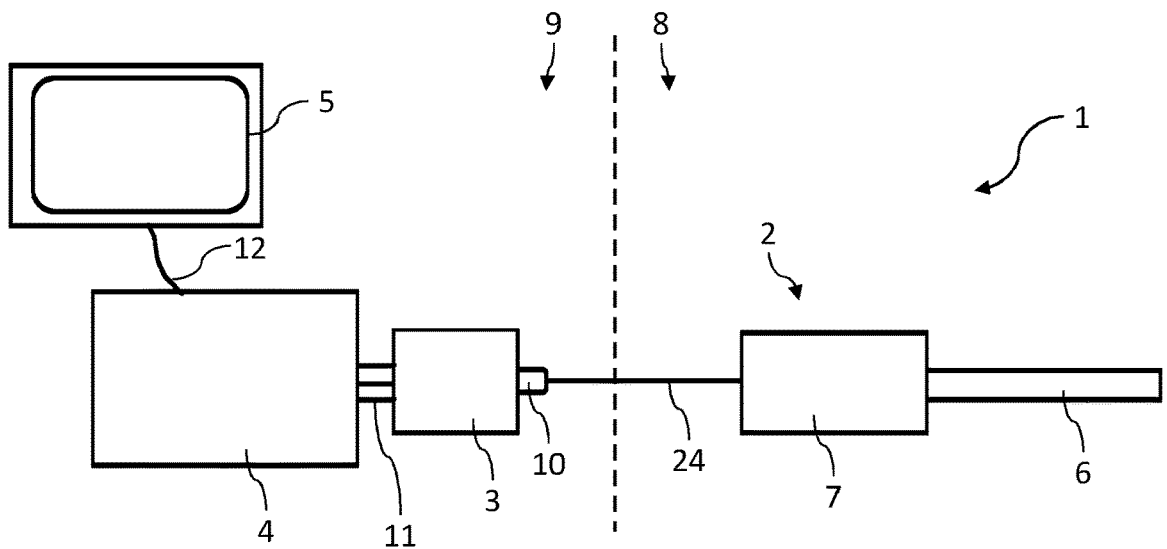
FIG. 1 shows an endoscope assembly with an endoscope, a combined image capturing and illumination unit, a control unit and an image display unit.

FIG. 1 shows an endoscope assembly 1 according to the invention with an endoscope 2, a combined image capturing and illumination unit 3, a control unit 4 and an image display unit 5.

Endoscope 2 has a shaft 6 and a handle 7. Inside shaft 6 and handle 7, an image guide and an optical waveguide are arranged, shown as image guide and optical waveguide unit 24 in the figure. As such, image guide 13 and optical waveguide 14 may each be composed of a fiber bundle including a plurality of image guide fibers or optical waveguide fibers.

The image guide may also be produced in a so-called extruding method in which the individual image fibers of the image guide are manufactured simultaneously and manual assembly of the fiber bundle is therefore not necessary. In particular, this allows to easily maintain the orientation of the individual image fibers so that the individual pixels of the image are correctly aligned. To increase image resolution, the image guide fibers may be elongated in an additional or alternative thermal process, enabling production of significantly thinner fibers.

In the figure, a sterile area 8 is separated from a non-sterile area 9 of a place of operation of endoscope assembly 1 by a dashed line. One advantage of the invention is that the image guide and, in the example, also the optical waveguide, may run uninterrupted in non-sterile area 9.

In non-sterile area 9, an image capturing and illumination unit 3 is arranged which has a combined image guide and optical waveguide interface 10 for connection to the image guide and the optical waveguide of endoscope 2.

Image capturing and illumination unit 3 has an image sensor and a light source. Image capturing and illumination unit 3 further has electrical interfaces 11 for connection to a control unit 4. In the example, this control unit 4 has a camera controller and an illumination controller. Control unit 4 has a data interface 12 for image output to an image display unit 5.

Figure 2:
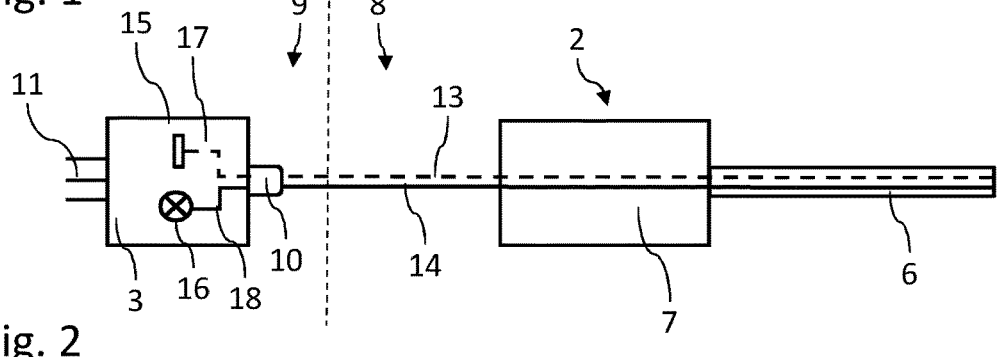
FIG. 2 shows an endoscope with a combined image capturing and illumination unit with a combined image guide and optical waveguide interface.

FIG. 2 shows an endoscope 2 with an image guide 13 and an optical waveguide 14, running uninterrupted to the proximal end in non-sterile area 9. There, they are connected to an image capturing and illumination unit 3 via a combined image guide and optical waveguide interface 10.

Image capturing and illumination unit 3 has an image sensor 15 which, in the example, is connected to the image guide and optical waveguide interface 10 with an internal image guide 17, so that an image of image guide 13 can be transmitted to image sensor 15.

Image capturing and illumination unit 3 has a light source 16 which, in the example, is connected to image guide and optical waveguide interface 10 via an internal optical waveguide 18, so that the light of light source 16 can enter optical waveguide 14. Finally, image capturing and illumination unit 3 has an electrical interface 11 for connection to a control unit 4.

Figure 3:
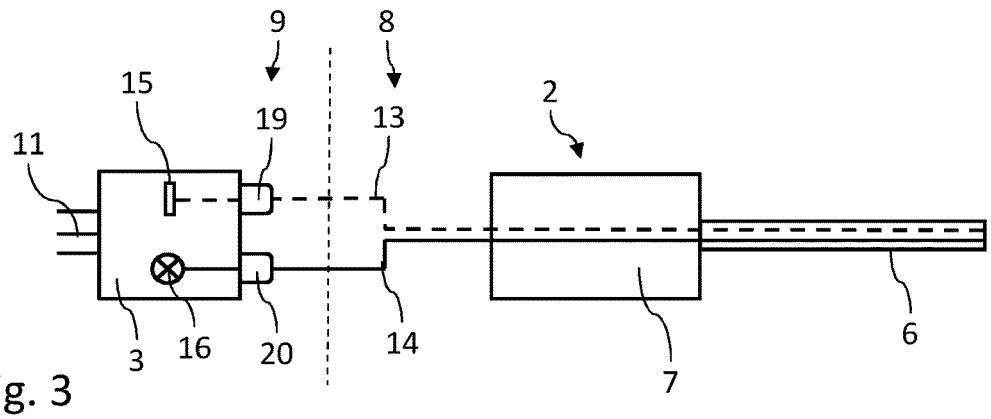
FIG. 3 shows an endoscope with a combined image capturing and illumination unit with separate image guide and optical waveguide interfaces.

The embodiment of FIG. 3 substantially corresponds to FIG. 2. However, image capturing and illumination unit 3 has a separate image guide interface 19 and a separate optical waveguide interface 20. As such, image sensor 15 is arranged in the area of image guide interface 19 such that an image of image guide 13 directly falls on image sensor 15 and an internal optical waveguide is not necessary.

Similarly, light source 16 is arranged in the area of optical waveguide interface 20, so that the light directly enters optical waveguide 14.

Figure 4:
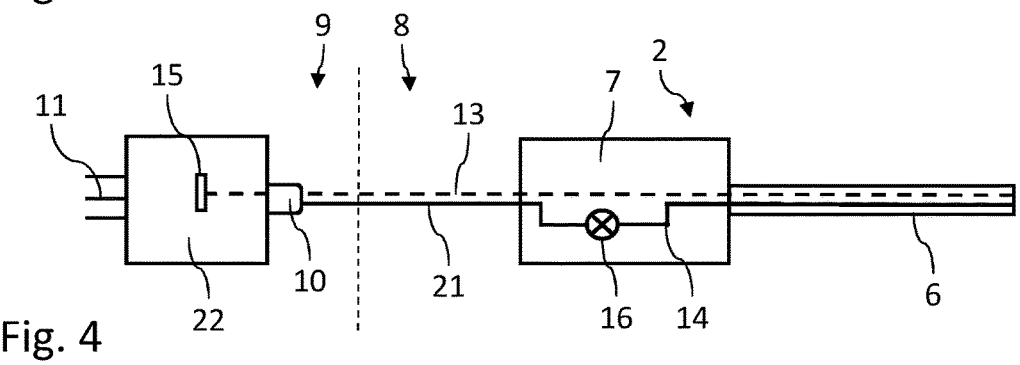
FIG. 4 shows an endoscope with an image capturing unit and an illumination unit integrated in the handle.

FIG. 4 shows an endoscope 2 and an image capturing unit 22 with an image sensor 15 in direct arrangement towards an image guide interface 19 as shown in FIG. 3. In this embodiment, a light source 16 is arranged in handle 7 of endoscope 2. Accordingly, in addition to image guide 13, an electric line 21 runs from endoscope 2 to image capturing unit 22. Hence, image guide interface 19 has an electrical interface for controlling the light source. Image capturing unit 22 further has an electrical interface 11 for connection to a control unit 4.

Figure 5:
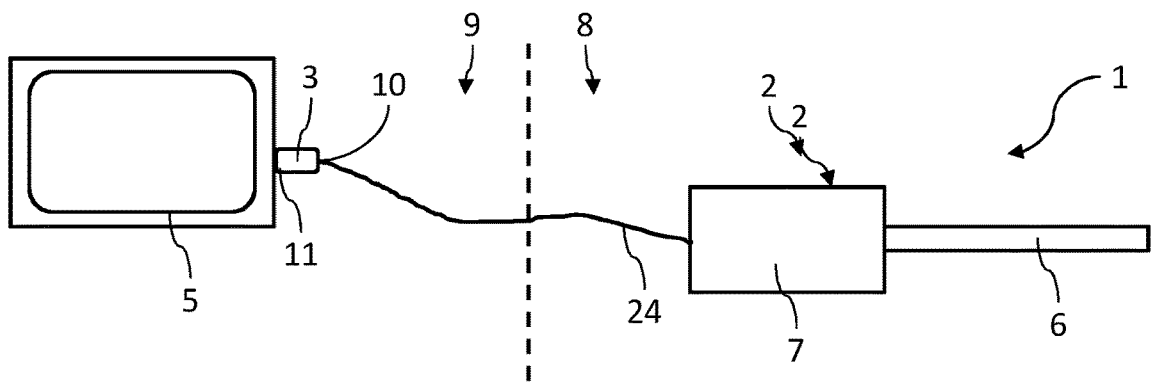
FIG. 5 shows an endoscope assembly with an endoscope, a combined image capturing and illumination unit as a USB drive and an image display unit.

FIG. 5 shows an alternative endoscope assembly 1 of FIG. 1. Here, electrical interface 11 of combined image capturing and illumination unit 3 is additionally configured for transmission of image signals, so that image capturing and illumination unit 3 is directly connected to an image display unit 5.

Figure 6:
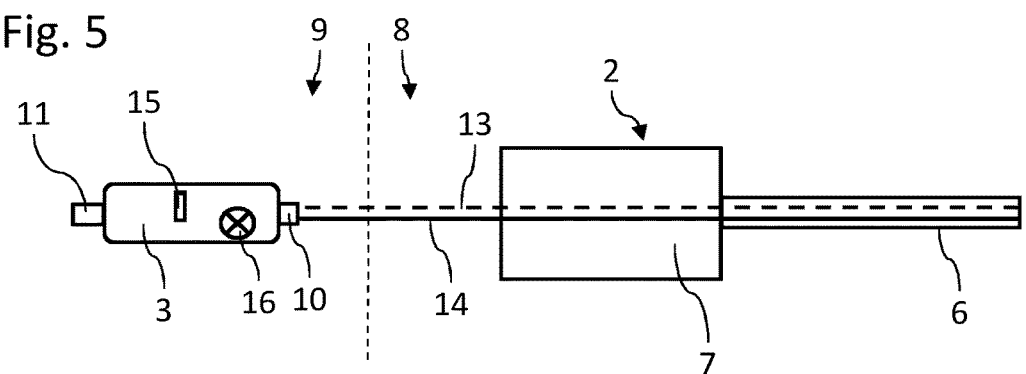
FIG. 6 shows an endoscope with a combined image capturing and illumination unit as a USB drive with a combined image guide and optical waveguide interface.
Figure 8:
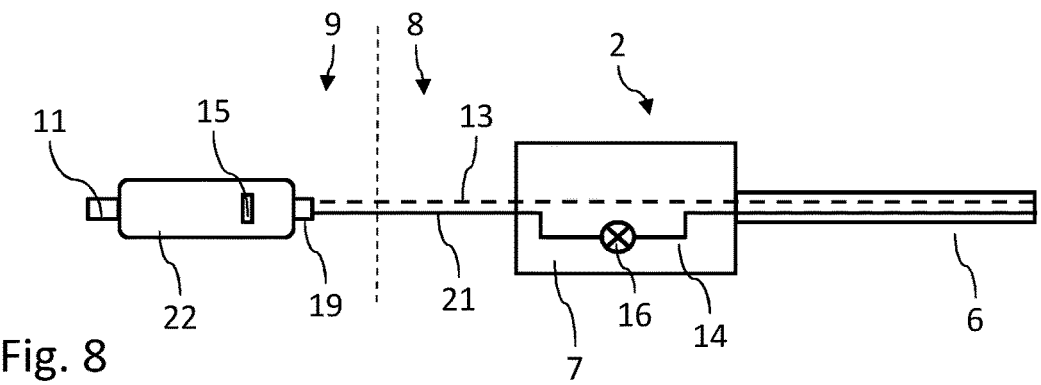
FIG. 8 shows an endoscope with an image capturing unit as a USB drive and an illumination unit integrated in the handle.

The embodiments of FIGS. 6 and 8 each substantially correspond to FIGS. 2 and 4. However, here, image capturing and illumination unit 3 is shown as a USB or media drive, the electrical interface 11 of which is configured as a media interface, e.g., as a USB and/or HDMI interface.

Figure 7:
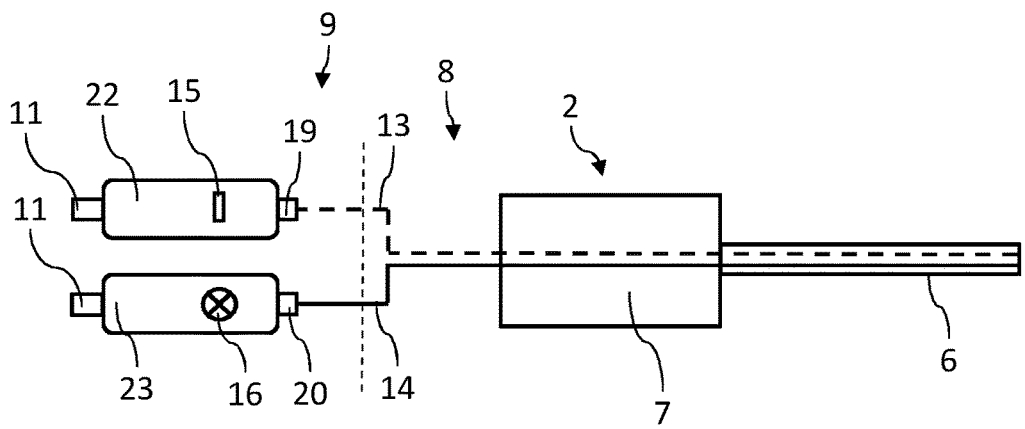
FIG. 7 shows an endoscope with a combined image capturing and illumination unit as a USB drive with separate image guide and optical waveguide interfaces.

The embodiment of FIG. 7 substantially corresponds to FIG. 3, in which an image capturing unit 22 and an illumination unit 23 are present in the form of a USB or media drive. Illumination unit 23 has an optical waveguide interface 24 for connection of optical waveguide 14.

Figure 9:
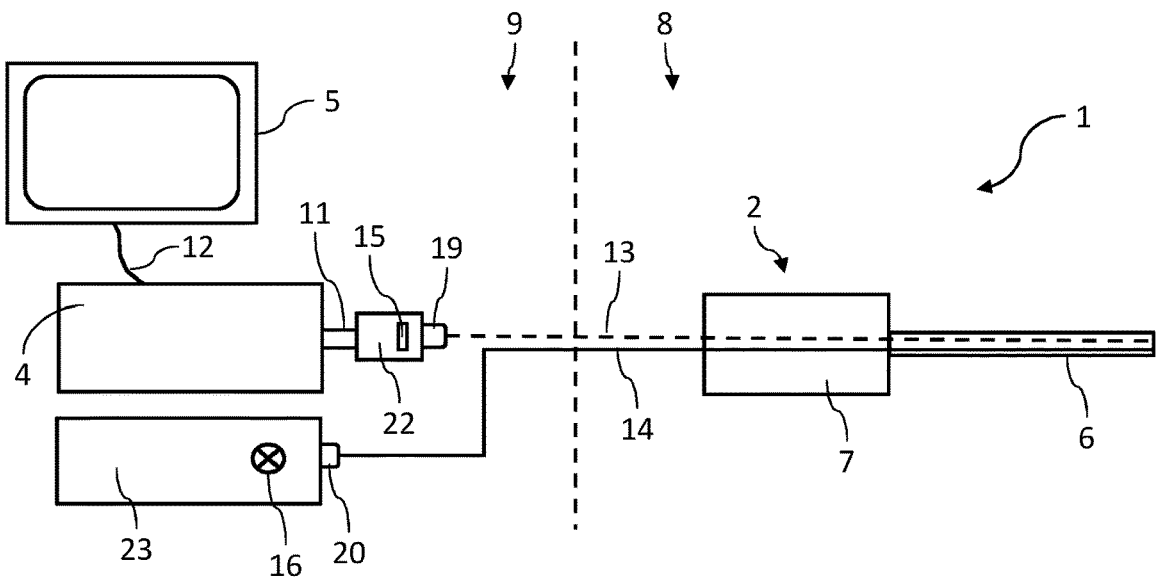
FIG. 9 shows an endoscope assembly with an endoscope, an image capturing unit coupled to a control unit, an illumination unit and an image display unit.

FIG. 9 shows an endoscope assembly 1 with an endoscope 2, an image capturing unit 22, an illumination unit 23, a control unit 4 and an image display unit 5. Image capturing unit 21 has an image guide interface 19 for connection to image guide 13 of endoscope 2 and an electrical interface 11 for connection to control unit 4. Illumination unit 23 is configured separately.

Figure 10:
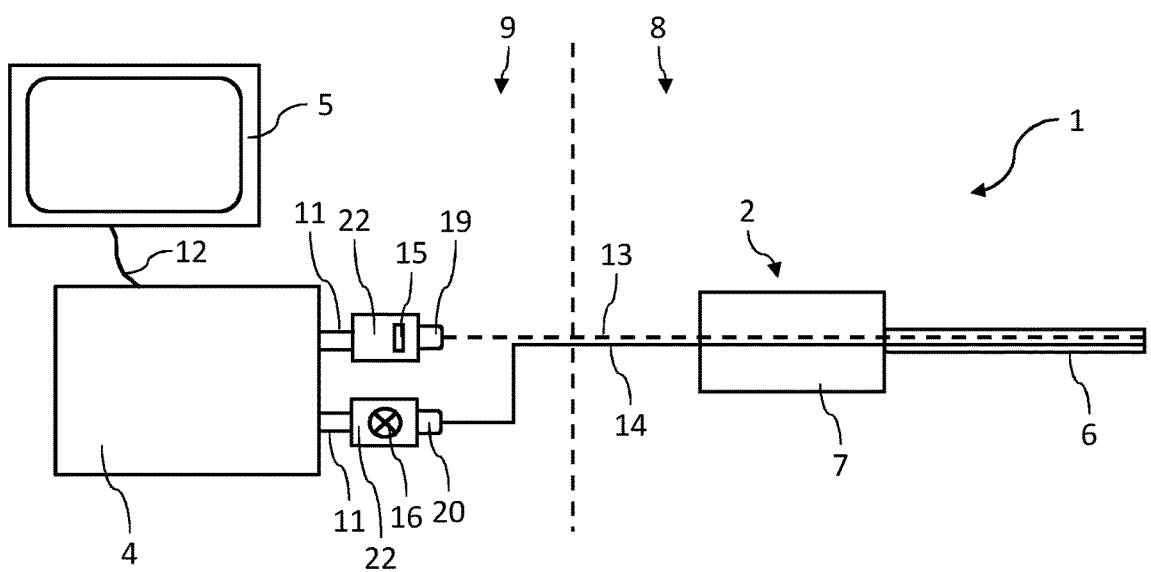
FIG. 10 shows an endoscope assembly with an endoscope, an image capturing unit and an illumination unit coupled to a control unit and an image display unit.

The embodiment of FIG. 10 differs from that in FIG. 9 in that illumination unit 23 also has an electrical interface 11 via which it is connected to control unit 4.

Figure 11:
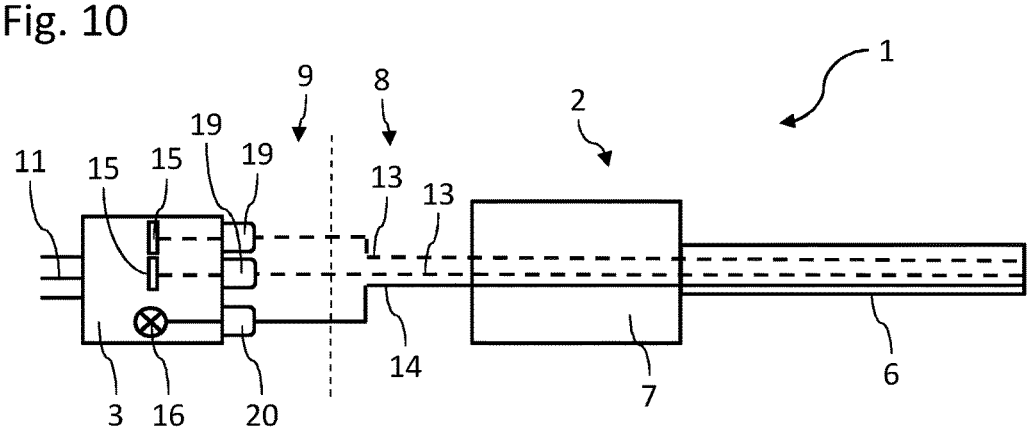
FIG. 11 shows an endoscope with two image guides and an optical waveguide, each connected to a combined image capturing and illumination unit.

FIG. 11 shows an endoscope 2 with two image guides 13 and an optical waveguide 14. Here, combined image capturing and illumination unit 3 accordingly has two image guide interfaces 19, each optically coupled to an image sensor 15. An electrical interface 11 enables connection to a control unit. In this embodiment, it is also basically possible to configure the electrical interface as a USB and/or HDMI interface.

What is claimed is:

1. An endoscope (2), comprising:
    an optical light guide (14); and
    an image guide (13) configured to run uninterrupted and without couplings up to the endoscope tip its proximal end, the image guide (13) having only a single image guide interface (10, 19) at its proximal end for optical connection to an external image capturing device (15);
    wherein no image sensor is arranged in the endoscope (2);
    wherein the endoscope (2) has a handle (7) and the image guide (13) passes through the handle (7), and extends outward from the handle (7), in particular at the proximal end of the handle (7), without interruption; and,
    wherein the only image guide interface (10, 19) is arranged distant from the handle (7) within a non-sterile area (9) of the endoscope (1), such that the handle (7) is free of an optical interface.

2. The endoscope according to claim 1, wherein the image guide (13) has at least one image guide fiber or at least one image guide fiber bundle.

3. The endoscope (2) according to claim 1, wherein the image guide interface has a coupling for optical and/or mechanical connection to an image capturing unit.

4. The endoscope (2) according to claim 1, wherein the endoscope (2) has a light source coupled to the optical light guide (14), or in that the optical light guide (14) is configured to be uninterrupted up to its proximal end and has an optical light guide interface at its proximal end for optical connection to an illumination unit.

5. An illumination unit (3, 22) for an endoscope assembly (1) comprising:
    a light source (16); and
    an optical light guide interface (20) for optical connection of the light source (16) to an optical light guide (14) and
    wherein the light guide interface (20) of the illumination unit (3, 22) is connected to the optical light guide (14) of an endoscope (2) according to claim 1.

6. The illumination unit (3, 22) according to claim 5, wherein the illumination unit (3, 22) further comprises an electrical interface (11) for controlling the light source (16).

7. An image capturing unit (3, 22) for an endoscope assembly (1) comprising:
    an image sensor (15); and
    an image guide interface (10, 19), for optical connection of the image sensor (15) to an external image guide (13); and
    wherein the image guide interface (10, 19) of the image capturing unit (3, 22) is configured for connection to the external image guide (13) of an endoscope (2) according to claim 1.

8. The image capturing unit (3, 22) according to claim 7, wherein the image guide interface (10, 19) with has a coupling for optical and/or mechanical connection to an external image guide (13), and the image guide interface of the endoscope (2) is coupled to the coupling of the image guide interface (10, 19) of the image capturing unit (3, 22).

9. The image capturing unit (3, 22) according to claim 7, wherein the image capturing unit (3, 22) further comprises an electrical interface (11) for controlling the image sensor (15) and/or for output of the image data of the image sensor (15).

10. An endoscope assembly (1) comprising:
    an image capturing unit (3, 22) according to claim 8,
    an illumination unit (23); and
    a sensor-less endoscope (2) according to claim 1, whose optical light guide (14) is connected to the illumination unit (23), and whose image guide (13) that is connected to the image capturing unit (3, 22).

11. The endoscope assembly (1) according to claim 10, wherein the optical light guide (14) of the endoscope (2) is configured to be uninterrupted up to its proximal end and has an optical light guide interface at its proximal end that is connected to the illumination unit (23), or wherein the endoscope has a handle (7) and the illumination unit (23) is arranged within the handle (7).

12. The endoscope assembly (1) according to claim 10, wherein the illumination unit (23) and/or the image capturing unit (3, 22) has/have an electrical interface (11) for connection to a control unit (4).

13. The endoscope assembly (1) according to claim 10, wherein the illumination unit (23) and/or the image capturing unit (3, 22) has/have an electrical interface (11), in particular USB and/or HDMI interface, for connection to an image display unit (5).

14. The endoscope assembly (1) according to claim 10, wherein the image capturing unit (3, 22) and the illumination unit (23) are arranged in one device.

15. The endoscope (2) according to claim 1, wherein the endoscope (2) is designed as a single-use endoscope (2) and thus does not require any cleaning or disinfecting after use.

16. An endoscope (2), comprising:
    an optical light guide (14); and
    an image guide (13) configured to run uninterrupted and without couplings up to the endoscope tip, the image guide (13) having only a single image guide interface (10, 19) at its proximal end for optical connection to an external image capturing device (15);

wherein no image sensor is arranged in the endoscope (2);

wherein the endoscope (2) has a handle (7) and the image guide (13) passes through the handle (land extends outward from the handle (7), in particular at the proximal end of the handle (7), without interruption;

wherein the only image guide interface (10, 19) is arranged distant from the handle (7) within a non-sterile area (9) of the endoscope (1), such that the handle (7) is free of an optical interface; and, wherein during a surgical procedure an endoscope (2) may be disconnected from the image guide interface (10, 19) and replaced with at least one additional endoscope (2) without the need for the performance of any sterilization steps.

* * * * *

UNITED STATES PATENT AND TRADEMARK OFFICE
CERTIFICATE OF CORRECTION

PATENT NO. : 11,589,741 B2
APPLICATION NO. : 17/094999
DATED : February 28, 2023
INVENTOR(S) : Stefan Schröer et al.

Page 1 of 1

It is certified that error appears in the above-identified patent and that said Letters Patent is hereby corrected as shown below:

In the Claims

Claim 1, Line 4, "its proximal end" should be deleted.

Claim 9, Line 2, "has" should be deleted.

Claim 17, Line 9, "(7and" should read as "(7) and".

Signed and Sealed this
Twenty-fourth Day of September, 2024

Katherine Kelly Vidal
*Director of the United States Patent and Trademark Office*